(12) United States Patent
Joanicot et al.

(10) Patent No.: US 8,053,242 B2
(45) Date of Patent: Nov. 8, 2011

(54) CRYSTALLIZATION OF CHEMICAL SPECIES/POLYMORPHS AND MICROFLUIDIC APPARATUS AND SCREENING METHODOLOGY THEREFOR

(75) Inventors: Mathieu Joanicot, Chatenay-Malabry (FR); Philippe Laval, Paris (FR); Jacques Leng, Bordeaux (FR); Jean-Baptiste Salmon, Bordeaux (FR)

(73) Assignee: Rhodia Operations, Aubervilliers Cedex (FR)

( * ) Notice: Subject to any disclaimer, the term of this patent is extended or adjusted under 35 U.S.C. 154(b) by 0 days.

(21) Appl. No.: 12/553,557

(22) Filed: Sep. 3, 2009

(65) Prior Publication Data
US 2010/0058845 A1    Mar. 11, 2010

Related U.S. Application Data

(63) Continuation of application No. PCT/FR2008/000288, filed on Mar. 5, 2008.

(60) Provisional application No. 60/905,022, filed on Mar. 5, 2007.

(51) Int. Cl.
*G01N 33/00* (2006.01)

(52) U.S. Cl. ........................................................ 436/86

(58) Field of Classification Search .................... 436/86
See application file for complete search history.

(56) References Cited

U.S. PATENT DOCUMENTS

| | | | |
|---|---|---|---|
| 7,214,540 B2 * | 5/2007 | DeLucas et al. ................ | 436/86 |
| 2005/0129580 A1 | 6/2005 | Swinehart et al. | |
| 2006/0137597 A1 | 6/2006 | David | |
| 2007/0052781 A1 | 3/2007 | Fraden et al. | |

FOREIGN PATENT DOCUMENTS
FR    2907228 A1    4/2008

OTHER PUBLICATIONS

Garcia et al., "Crystallization and dissolution of pharmaceutical compounds: An experimental approach", Journal of Crystal Growth, 198/199, 1360-1364 (1999).*

* cited by examiner

*Primary Examiner* — Jill Warden
*Assistant Examiner* — Monique Cole
(74) *Attorney, Agent, or Firm* — Buchanan Ingersoll & Rooney, P.C.

(57) ABSTRACT

The crystallization of chemical species/polymorphs comprises forming droplets of a solution of a substance with optionally different concentrations of said substance in an inert phase; producing and storing the droplets in at least one storage microchannel (1); forming crystals in all droplets; increasing the temperature in order to induce the dissolution of at least a portion of the crystals in at least some droplets; and analyzing the crystallization and dissolution process.

21 Claims, 3 Drawing Sheets

CRYSTALLIZATION OF CHEMICAL SPECIES/POLYMORPHS AND MICROFLUIDIC APPARATUS AND SCREENING METHODOLOGY THEREFOR

CROSS-REFERENCE TO PRIORITY/PROVISIONAL APPLICATIONS

This application claims priority under 35 U.S.C. §120 of U.S. Provisional Application No. 60/905,022, filed Mar. 5, 2007, and is a continuation/national phase of PCT/FR 2008/000288, filed Mar. 5, 2008 and designating the United States (published in the French language on Nov. 6, 2008 as WO 2008/132309 A2; the title and abstract were also published in English), each hereby expressly incorporated by reference in its entirety and each assigned to the assignee hereof.

BACKGROUND OF THE INVENTION

1. Technical Field of the Invention

The present invention relates to methodology and microfluidic apparatus/device for monitoring the crystallization of a substance and to a screening protocol comprising such methodology.

This invention more particularly features, but not exclusively, the study of polymorphism, namely, the possibility that a given molecule crystallizes in different crystalline structures without however changing chemical composition. The various crystalline forms that can be adopted by this molecule are called polymorphs.

2. Description of Background and/or Related and/or Prior Art:

The fact of predicting which polymorph is likely to crystallize is of great importance in chemical and pharmaceutical processes, insofar as each polymorph of a given substance has specific physical properties. Compare the following publications: J. Bernstein, *J. Phys. D. Appl. Phys.*, 26, 66 (1993); K. Sato, *J. Phys. D. Appl. Phys.*, 26, 77 (1993); and J. Bernstein, J. Davey and J. O. Henck, Angew. *Chem. Int. Ed.*, 88, 3440 (1999).

However, complete understanding of the complexity of the process of crystallization in solution is lacking from the prior art. Such a lack is in particular due to existing links from the thermodynamic characteristics of phase diagrams and the kinetics of phase transitions (particularly nucleation), to the experimental difficulties in obtaining reliable and reproducible measurements, because of the presence of impurities, and to the large number of parameters, such as the pH, the temperature or the presence of solvent, which play an important role. To illustrate the latter point, see the following publications: J. W. Mullin, Crystallisation (Butterworth-Heinemann, Oxford, 2001); A. C. Zettlemoyer, Nucleation (Marcel Dekker, New York, 1969); N. Rodriguez-Hornedo and D. Murphy, *Journal of Pharmaceutical Sciences* 88, 651 (1999); D. Kashchiev, D. Clausse and C. Jolivet-Dalmazzone, *J. Colloid Interface Sci.*, 165, 148 (1994).

High-flow-rate techniques are likely to improve this understanding, by providing the possibility of greater screening of the crystallization conditions. In addition, microfluidics appears to be a good gateway for such experiments, insofar as it offers very precise control, through the design of specific kinetic pathways in phase diagrams. With regard to the latter aspect, refer to the following publications: C. L. Hansen, S. Classen, J. M. Berger and S. R. Quake, *J. Am. Chem. Soc.*, 128, 3142 (2006); J. Leng, B. Lonetti, P. Tabeling, M. Joanicot and A. Ajdari, *Phys. Rev. Lett.*, 96, 084503 (2006); C. J. Gerdts, V. Tereshko, M. K. Yadav, I. Dementieva, F. Collart, A. Joachimiak, R. C. Stevens, P. Kuhn, A. Kossiakoff and R. F. Ismagilov, *Angew. Chem. Int. Ed. Engl.*, 45, 8156 (2006).

In addition, microfluidics offer the possibility of screening a very large number of physico-chemical systems using very small amounts of compounds, typically varying from the range of nanoliters (nl) to microliters (µl). With regard to the latter point, namely the "Lab on chip" technology, also compare the following publications: C. L. Hansen, E. Skordalakee, J. M. Berger and S. R. Quake, *Proc. Natl. Acad. Sci., USA* 99, 16531 (2002); D. L. Chen and R. F. Ismagilov, *Current Opinion in Chemical Biology*, 10, 226 (2006); K. Shinohara, T. Fukui, H. Abe, N. Sekimura and K. Okamoto, Langmuir 22, 6477 (2006); B. Zheng, J. D. Tica, L. S. Roach and R. F. Ismagilov, Angew. *Chem. Int. Ed.*, 43, 2508 (2004).

SUMMARY OF THE INVENTION

Accordingly, the present invention features a method for understanding, in a more precise manner than in the prior art, crystallization phenomena.

Thus, the present invention features a method of monitoring the crystallization of a substance in solution in a solvent, comprising the following steps:

droplets of said solution, optionally with different concentrations of said substance, are formed in an inert phase;

the droplets are produced and stored in at least one storage microchannel;

crystals are formed in all the droplets;

the temperature is increased so as to dissolve at least some of the crystals in at least some droplets; and the crystallization and dissolution process is observed by analyzing means.

One embodiment of the invention is a method of monitoring the crystallization of a substance in solution in a solvent, comprising the following steps:

droplets of the solution, optionally with different concentrations of the substance, are formed in an inert phase;

the droplets are produced and stored in at least one storage microchannel;

crystals are formed in all the droplets, the volume of each droplet being small enough to induce a single-nucleation crystallization mechanism, in at least most of the droplets; and at least two different crystalline structures are observed for the same substance, in at least two different droplets.

This invention may include at least certain of the following features, compatible with one or other of the definitions provided above:

the droplets are formed at a temperature above the solubility temperature of said substance;

crystals are formed in all the droplets by cooling these droplets below the solubility temperature;

the analysis means comprise Raman spectroscopy or optical microscopy;

the method according to the invention includes an additional step of observing the structure of the crystals formed during the crystallization, especially by Raman spectroscopy;

the method according to the invention includes the observation of at least two different crystalline structures for the same substance, because of the polymorphism determination;

at least one hundred droplets, preferably at least two hundred droplets, are formed;

the volume of each droplet formed is small enough to induce a single-nucleation crystallization mechanism in at least most of the droplets;

the volume of each droplet formed is less than 1 µl, preferably less than 0.2 µl;

the inert phase is a silicone oil or a fluorinated oil;

the solubility is measured as a function of the temperature of a metastable polymorph or of several polymorphs at the same time;

the temperature of the droplets is lowered and/or raised in steps;

the temperature difference per step is from 0.1 to 5° C., preferably from 0.5 to 1° C.;

the number of steps is from 10 to 50, especially from 20 to 30;

a first temperature, for which all the crystals are formed, is identified;

the temperature is lowered in steps, the number of crystals for different temperature values is counted and said first temperature is determined as being the temperature below which no additional crystal is formed;

a second temperature, for which all the crystals are dissolved, is identified; and the temperature is increased in steps, the number of crystals for increasingly higher temperatures is counted and said second temperature is identified, this being the temperature above which no additional crystal dissolves.

Another embodiment of the invention is a microfluidic device/apparatus for monitoring the crystallization of a substance in solution in a solvent, comprising:

at least one storage microchannel for storing droplets of said solution in an inert phase;

a first inlet for introducing said solution into said storage microchannel;

a second inlet for introducing said inert phase into said storage microchannel; and means for closing said storage microchannel, said means being placed downstream of this storage channel.

According to other features of the invention:

the device according to the invention further includes means for heating and cooling the droplets stored in the storage microchannel;

the storage microchannel has an equivalent diameter of from 50 µm to 1 mm, preferably from 400 to 600 µm;

the storage microchannel is formed in a material selected from elastomer materials, such as a silicone, more particularly such as PDMS, glass, silicon, PMMA and photosensitive resins;

the means for heating and cooling the droplets comprise a Peltier module;

the device according to the invention further includes an additional inlet for introducing an additional amount of said inert phase or of a second inert phase, which is not miscible with said inert phase, so as to space the droplets apart and prevent them from coalescing;

the device according to the invention further includes an outlet placed from the first and second inlet and the storage microchannel; and the device according to the invention further includes another additional inlet for introducing an additional amount of the solvent phase of the solution into the storage microchannel, this other additional inlet being located from the first and second inlet and the storage microchannel.

A final embodiment of the invention is a method of screening several substances, in which said several substances are prepared, the crystallization of each substance is monitored using the method as defined above, and at least one preferred substance, among said several substances, is identified.

According to other features of the invention:

said several substances are prepared by modifying at least one parameter of these substances, selected in particular from the pH, the presence of impurities or the presence of at least one adjuvant; and said several substances are formed from a mixture of at least two components and said different substances are prepared by modifying the proportion of these components.

BRIEF DESCRIPTION OF THE DRAWINGS

The invention will be described below with reference to the appended drawings, given solely by way of non-limiting example, in which.

DETAILED DESCRIPTION OF BEST MODE AND SPECIFIC/PREFERRED EMBODIMENTS OF THE INVENTION

The storage device according to the invention, illustrated in FIGS. 1 and 2, firstly comprises at least one microchannel 1, suited for storing a succession of droplets as will be seen later. This microchannel 1 is for example etched in a sheet 10, more particularly visible in FIG. 2, using conventional procedures of the prior art. In this regard, see, in particular, the publication by "D. C. Dussy, J. C. Macdonald, J. Olivier, A. Schueller and Georges M. Whitesides, *Anna. L. Chem.*, 70, pp. 4974-4984, (1998)".

The constituent materials of this sheet are for example selected from glass, which is a preferred material, and elastomer materials, such as silicones. It is also possible to employ sheets of PDMS (polydimethylsiloxane), silicon, PMMA (polymethyl methacrylate) or photosensitive resins. The microchannel may be of any appropriate shape, for example of circular or transverse cross section. The transverse dimension, such as the diameter in the case of a circular microchannel, advantageously ranges from 50 µm to 1 mm, preferably from 400 to 600 µm.

The storage device further includes an inlet 2 for introducing an inert phase into the microchannel 1 and an inlet 3 for introducing, into this microchannel, the solution whose crystallization is to be studied. The inlet 2 is joined to two microchannels 7 forming, in a known manner, a square pattern, which are joined at their intersection with an additional microchannel 8, in communication with the inlet 3. Thus, after this intersection, these various microchannels 7 and 8 emerge in a microchannel 9, called a linking microchannel, which is itself in communication with the inlet of the storage microchannel 1.

In addition, at the end of the microchannel 1 on the opposite side from the inlets 2 and 3, closure means 4 are provided for closing off this storage microchannel 1, namely, for stopping the advance of the solution within this microchannel 1. Such closure means are for example formed by a valve of any suitable type.

Finally, an additional inlet 5 is provided for introducing an additional amount of inert phase or a second inert phase of different nature, which is immiscible with the first inert phase. As will be seen later, this makes it possible, where appropriate, to separate the droplets and thus prevent them from coalescing. This additional inlet 5 is associated with an outlet 6, both of these being in communication with the linking microchannel 9.

Figure 2:
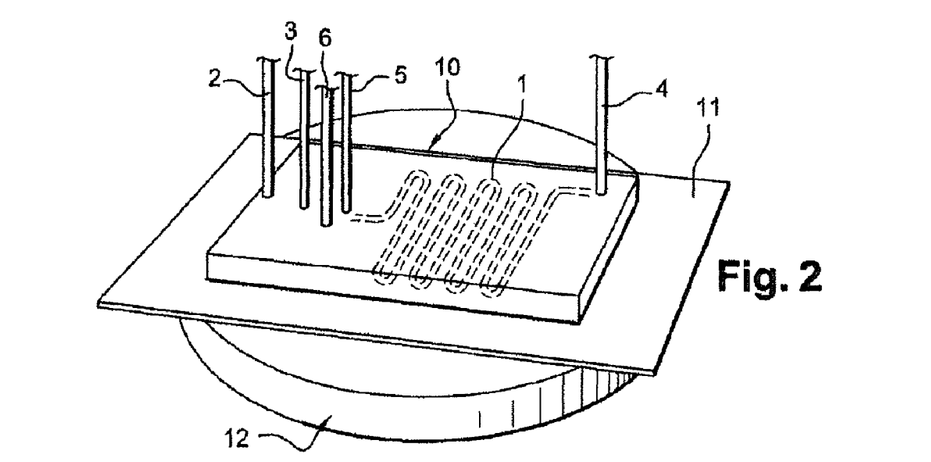
FIG. 2 is a perspective view illustrating the installation according to the invention.

As shown in FIG. 2, the various microchannels are blocked off by means of a plate 11, in a manner known per se. This plate 11, which is for example made of silicon, is associated with means for heating and cooling the droplets stored in the microchannel 1. These means for varying the temperature comprise for example a Peltier module, of a type known per se. This module is illustrated schematically in FIG. 2, where it is assigned the reference 12.

Each of the inlets 2, 3 and 5 and the outlet 6 are designed to receive one end of a tube, the other end of which is connected to a syringe.

The flow rate of each administered component is controlled by means of a syringe plunger. These tubes, syringes and syringe plungers are well known in the prior art, so they will not be further described.

The installation further includes means for observing at least part of the storage microchannel 1. These means (not shown) are for example a microscope. In addition, means are provided for analyzing the droplets contained in the storage microchannel. Such analyzing means are for example formed by a Raman spectrometer, also not shown.

The purpose of the present invention is to study a solution comprising a solvent and a substance capable of crystallizing in various forms, namely capable of generating polymorphs. To provide an example, this solution may be formed by potassium nitrate ($KNO_3$) in water.

Each polymorph is associated with a corresponding solubility temperature. The temperature below which all the polymorph forms are crystallized is called the minimum temperature ($T_{min}$) and the temperature above which all the polymorph forms are dissolved is called the maximum temperature ($T_{max}$).

Figure 3:
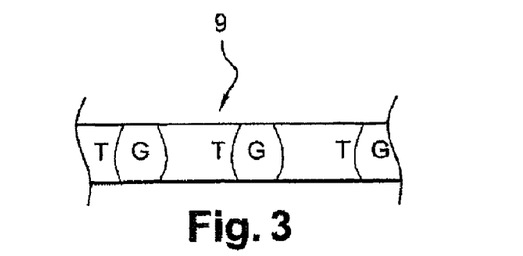
FIG. 3 is a front view, on a larger scale than FIG. 1, illustrating the formation of droplets.

Droplets of this solution are firstly formed in an inert phase. For this purpose, the solution is introduced via the inlet 2 and the inert phase, which is for example silicone oil, is introduced via the inlet 3. Downstream of the intersection, namely, in the linking microchannel 9, a train of droplets G, separated by portions T of carrier phase (see FIG. 3), is formed in a manner known per se. Advantageously, the volume of each droplet G is less than 1 µl, preferably less than 0.2 µl. As will be seen in greater detail hereafter, this small volume makes it possible to induce a single-nucleation crystallization mechanism in most of the droplets.

After the droplets have been formed, as described above, they are introduced into the storage microchannel 1 at a temperature above the aforementioned temperature $T_{max}$. Thus, all the products are in soluble form such that there is no risk of obstructing the microchannel. It should be noted that this temperature $T_{max}$ is possibly known for the concentration value relating to the initially injected solution. However, this temperature may not be known for other concentration ranges.

Next, when a sufficient number of droplets is present in the microchannel 1, in particular when the entire microchannel is occupied by the droplets, the valve 4 is closed. Under these conditions, the train of droplets is immobilized within the storage microchannel 1. Advantageously, at least one hundred droplets, preferably at least two hundred droplets, are present in this storage microchannel 1. To achieve such a number, it is possible to adjust the size of the droplets and/or the length of the flow microchannel. The presence of a large number of droplets is advantageous, as a large number of polymorphs may be viewed.

Next, crystals are formed in all the droplets. For this purpose, thanks to the Peltier module, the temperature is progressively lowered to a temperature below the aforementioned temperature $T_{min}$. This lowering in temperature takes place in steps, as illustrated in FIG. 4.

This temperature-lowering profile may be described by means of two main characteristics:
 the value of each step, namely, the drop in temperature $\Delta T$ at each step; and
 the total number N of steps.

Figure 6:
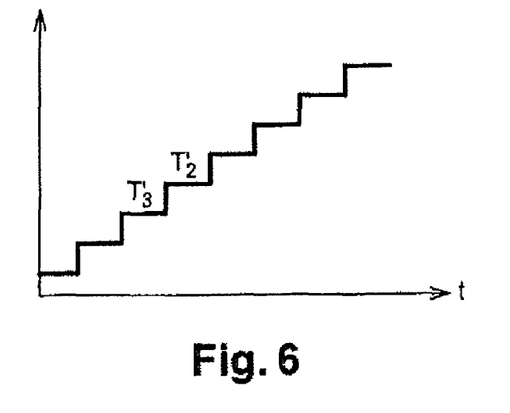
FIG. 6 is a graph, similar to FIG. 4, illustrating a rise in temperature of the solution, implemented in accordance with the invention.

Advantageously, $\Delta T$ ranges from 0.1 to 5° C., preferably from 0.5 to 1° C., while the number N of steps ranges from 10 to 50, preferably from 20 to 30. It should be noted that FIGS. 4 and 6 illustrate a much smaller number of steps, such as not to burden the drawings. As the temperature is progressively lowered, the user looks for the possible presence of crystals in the substance and, if they are present, he estimates the number of these crystals.

Figure 4:
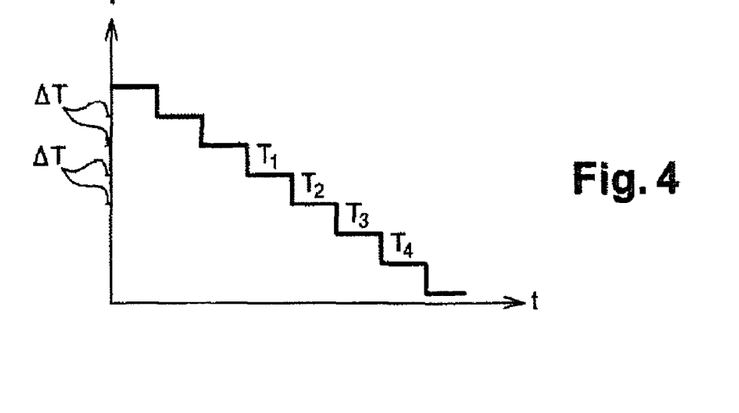
FIG. 4 is a graph illustrating a drop in temperature of a solution implemented using a method according to the invention.

Thus, referring to FIG. 4, the substance being studied is observed for four temperatures denoted by $T_1$ to $T_4$. This figure shows that the first crystals appear at $T_1$, that a larger number is present at $T_2$ and a much higher number of crystals at $T_3$. Finally, at $T_4$ the number of crystals has not increased substantially, compared with the temperature $T_3$. Under these conditions, it may be concluded that $T_3$ corresponds to the aforementioned temperature $T_{min}$.

Figure 5:
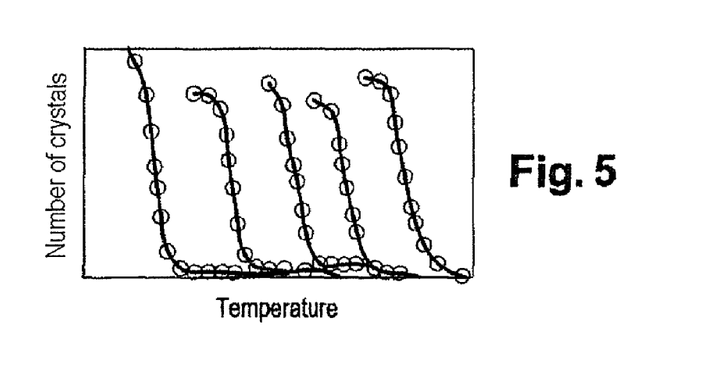
FIG. 5 is a graph illustrating the number of crystals present, as a function of temperature, for various concentrations of the solution.

It is also possible to plot a curve illustrating the number of crystals present as a function of temperature. Several similar curves may be plotted for various concentrations. FIG. 5 illustrates five of these curves, denoted by $C_1$ to $C_5$, for various concentration values. For each of these curves, as the temperature progressively increases, the number of crystals present is initially very high but it then very rapidly decreases before stabilizing to a zero value. It has also been found that the higher the concentration, the lower the temperature at which the crystals appear.

The temperature is then decreased for example to two to three degrees below temperature $T_{min}$ defined above, so as to ensure that all the droplets have crystallized. The temperature is conversely increased according to the profile illustrated in FIG. 6. As when the temperature was lowered, this rise takes place in steps, the value and the number of which are for example identical to those of the lowering phase.

In this temperature rise, various observations are made on the droplets so as identify any dissolution of the initially formed crystals and, if dissolution takes place, to determine the number of these dissolved crystals. Thus, at a temperature denoted by $T'_3$, it is found that only some of the crystals have dissolved.

However, at a higher temperature, denoted by $T'_2$, additional crystals have dissolved starting from this intermediate temperature $T'_3$. From this it may be concluded that two types of different crystals are present, associated with different dissolution temperatures. It should be noted that the temperatures $T'_3$ and $T'_2$, which correspond to the temperature rise, are different from the temperatures $T_2$ and $T_3$ relating to the temperature lowering illustrated in FIG. 4.

Finally, if the temperature continues to rise above $T'_2$, it is observed that all the crystals at the temperature $T_{max}$ as defined above have dissolved. Thus, it should be noted that this temperature rise is used to check the value of this temperature $T_{max}$ if it is already known, or else to determine this temperature if it is not known, for example if the concentration is varied.

Figure 7:
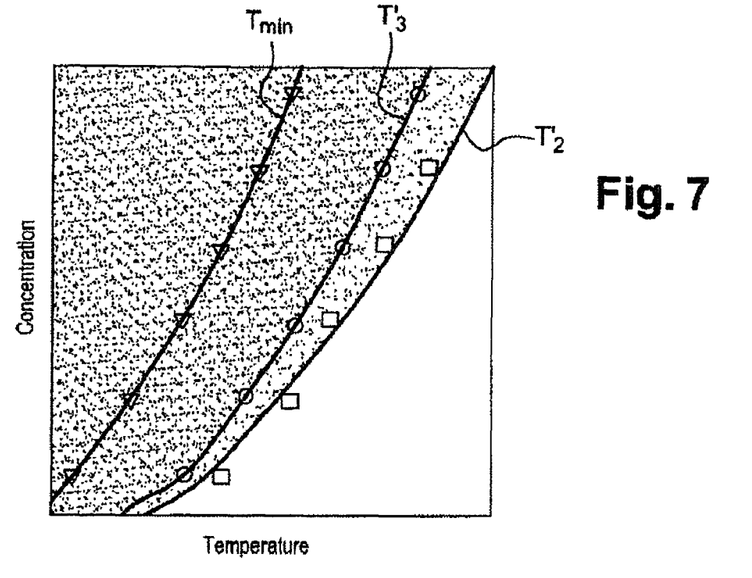
FIG. 7 is a graph illustrating various solubility curves of the solution.

FIG. 7 illustrates the variations, as a function of the concentration c, of the temperatures $T_{min}$, $T'_3$ and $T'_2$. $T_{min}$ corresponds to the estimate of the metastability limit of the system for small reactor volumes, such as the droplets used in the invention. This value $T_{min}$ is of considerable importance for optimizing a crystallization process, in particular in terms of morphology, size and size distribution.

The variation of $T'_2$ as a function of the concentration corresponds to the potassium nitrate solubility curve given in the literature (see D. R. Lide, Handbook of Chemistry and Physics, (CRC Press, 2004-2005)). However, the presence of a curve $T'_3$ as a function of the concentration indicates the presence of a metastable polymorph, the solubility of which is higher than the stable state at a given temperature. Consequently, the system is monotropic and concomitant, within the meaning given in J. Bernstein, J. Davey and J. O. Henck, Angew. Chem. Int. Ed., 88, 3440 (1999).

To confirm whether these two identified forms do actually have different crystalline structures, spectroscopic measurements were carried out on the crystals, directly within the droplets. For this purpose, a Raman microscope of the HR/Jobin-Yvon Lab Ram type can be used, the excitation wavelength of which is 532 nm and the objective is 10×. The curves shown in FIGS. 8 and 9 correspond to the temperatures $T'_2$ and $T'_3$ respectively.

Figure 8:
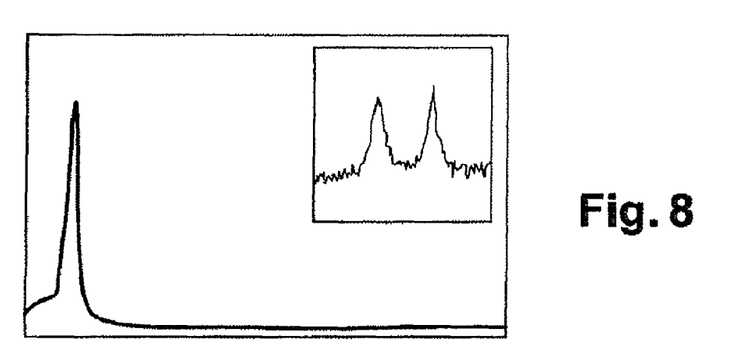
FIGS. 8 and 9 are graphs illustrating Raman spectra of two different crystals, isolated per the invention.
Figure 9:
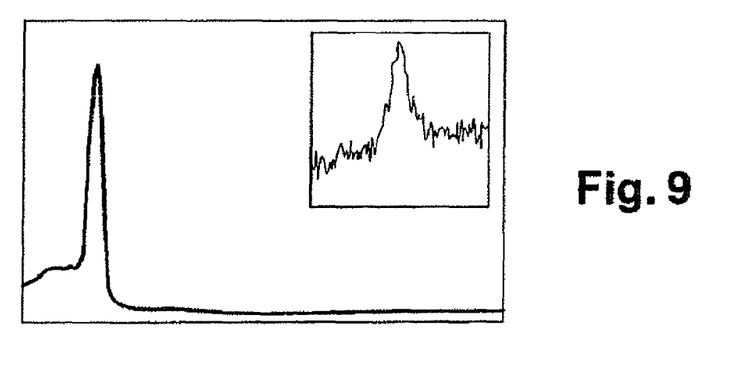

The vibration frequencies $V_1$, $V_3$ of the covalent modes of $NO_3^-$ make it possible to identify the form, which dissolves at the temperature $T'_2$, as being the stable form of $KNO_3$, namely, the II state. In addition, the form that dissolves at $T'_3$ corresponds to the ferroelectric polymorph, called III state. As regards the latter point, refer to the following publications: Frankenheim, Ann. Physik 40, 447 (1837); F. C. Kracek, J. Phys. Chem., 34, 225 (1930); J. K. Nimmo and B. W. Lucas, Acta Cryst., B32, 1968 (1976); C. N. R. Rao, B. Praskash and M. Natarajan, Nat. Stand. Ref. Data. Ser., U.S. Nat. Bur. Stand. 53, 1 (1975).

The III state is known to appear when specific temperature cycles are carried out at atmospheric pressure on simple $KNO_3$ crystals. In this regard, refer to the following publications: M. Balkanski, M. K. Teng and M. Nusimovici, Phys. Rev., 176, 1098 (1968); M. H. Brooker, J. Phys. Chem. Solids, 39, 657 (1978); R. Murugan, P. J. Huang, A. Ghule and H. Chang, Thermochimica Acta., 346, 83 (2000).

Thus, when the stable crystals are heated above 130° C. they initially undergo a transformation to a rhombohedral structure (I state). Next, upon cooling, they are converted to the III state, which seems to be stable within the 110 to 120° C. range, before returning again to the III state at low temperatures. This means that the transition from the III state and the II state takes place over a wide temperature range, which means that the III state may be detected as a metastable state at room temperature. The present invention thus makes it possible to observe the nucleation in solution of this metastable form.

As is apparent from the foregoing, this invention makes it possible to measure the solubility curve of metastable polymorphs, such as the III state of $KNO_3$ in solution. The solubility of this type of polymorph cannot in general be characterized using the methods of the prior art.

Without wishing to be tied to a particular theory, it is assumed that this possibility of obtaining metastable states is in particular permitted by the fact that, in the droplets used, essentially no multiple nucleation takes place. In other words, the crystallization mechanism is a single-nucleation mechanism, that is to say, it involves a single nucleation phenomenon.

Under these conditions, even when a polymorph is metastable, it subsequently does not transform to a more stable state. Now, the methods of the prior art are generally accompanied by such multiple nucleation so that the metastable polymorph cannot be studied, because it transforms to a more stable polymorph immediately after its appearance. In other words, in the prior art, the metastable polymorphs have an extremely short life time so that they cannot be studied.

In this regard, it will be noted that the fact of using droplets of small volume is advantageous, as it avoids any multiple nucleation. In addition, the fact of using droplets separated by portions of inert phase prevents any interactions from the various crystals. It will also be noted that the invention avoids having to use stirring, which is likely to induce multiple nucleations.

Finally, in accordance with the present invention, many individual crystals can be studied, thereby enabling the various solubilities to be efficiently determined when different polymorphs exist. In addition, the means for varying temperature used in the invention allow this temperature to be set reliably and uniformly, thereby distinguishing from polymorphs having solubilities that are close together.

Figure 10:
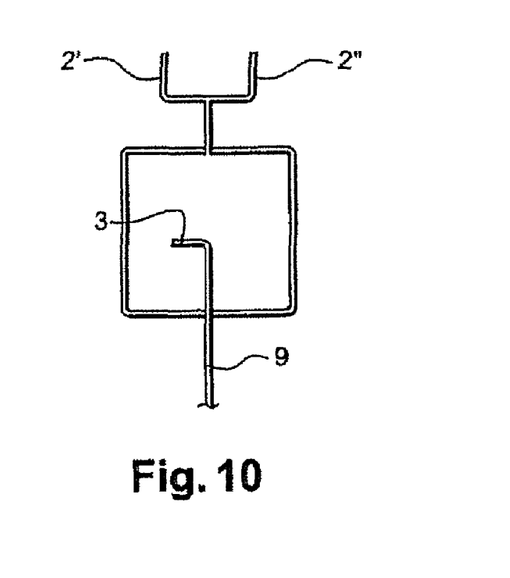
FIG. 10 is a front view, on a larger scale than FIG. 1, illustrating an alternative embodiment of the invention.

Another embodiment of the invention is illustrated with reference to FIG. 10. In this embodiment, a method for screening various substances is carried out.

For this purpose, the various substances are firstly prepared. Thus, the single inlet 2 is replaced, in the example illustrated, by two inlets 2' and 2" into each of which a component is injected. The substance which is studied is therefore formed by the mixture of these two components.

A first substance is prepared, which is studied in accordance with the method described above. At least one parameter is then modified, so as to modify the composition of this substance. To provide a non-limiting example, these parameters are in particular the concentration of each component within the substance, the pH, or else the possible presence of impurities. After having studied the various substances thus prepared, one or more preferred substances, in particular according to the intended application, are determined.

According to a variant embodiment (not shown), each substance may be formed from at least three components. Under these conditions, a corresponding number of inlets, similar to those 2' and 2", is provided.

The invention is not limited to the examples described and illustrated.

Thus, in the above embodiment, the temperature is lowered and raised according to respective stepped profiles. However, the temperature may be lowered and/or raised using different profiles, such as, in particular: a single-step profile; a continuously increasing or decreasing profile; successive temperature lowering and raising steps.

According to another embodiment of the invention, it is possible to carry out just one crystallization phase, without subsequent dissolution. Under these conditions, during crystallization, which takes place in particular by lowering the temperature, according to one or another of the variant embodiments presented above, crystals are formed, a single crystal being present per droplet, for most of the droplets. For this purpose, droplets of very small volume are produced, as indicated above. Once these crystals have formed, the possible polymorphs are then identified.

Thus, in the latter immediately previous variant embodiment, this invention features a method of monitoring the crystallization of a substance in solution in a solvent, which comprises the following steps:

droplets of the solution, optionally with different concentrations of the substance, are formed in an inert phase;
the droplets are produced and stored in at least one storage microchannel;
crystals are formed in all the droplets, the volume of each droplet being small enough to induce a single-nucleation crystallization mechanism in at least most of the droplets; and
at least two different crystalline structures are observed for the same substance, in at least two different droplets.

The above features may be combined with any other feature, described in the present application, which is technically compatible therewith.

Figure 1:
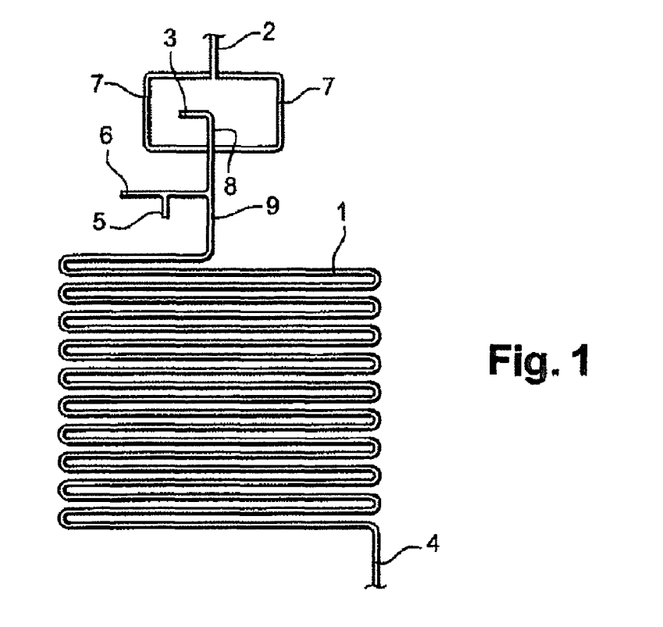
FIG. 1 is a front view illustrating a flow device belonging to an installation according to the invention.

One exemplary embodiment of the invention will now be given:

The microfluidic device, as described in FIGS. 1 and 2, was made of PDMS using standard lithography techniques, as described in J. C. Mcdonald and G. M. Whitesides, *Account of Chemical Research* 35, 491 (2002). The height and the width of the channels was 500 μm. The PDMS device was sealed by means of a silicon plate so as to increase heat transfer.

The inert phase (Rhodorsil 20 CST silicone oil) and the aqueous solution ($KNO_3$, from Normapur Merck, in deionized water) were injected at controlled flow rates, using syringe plungers. Monodisperse aqueous droplets were formed in the linking microchannel 9. Typical flow rates of 1800 to 600 μl per hour, for the inert phase and aqueous phase respectively, produced droplets within the 100 to 200 nanoliter range. An additional inert phase could also be injected, via the inlet 5, so as to push the droplets apart and avoid any coalescence during their storage.

The outlets 4 and 6 shown in FIG. 1 were connected to tubes, which could be closed by means of computer-controlled pinch valves. Initially, the outlet 6 was closed and the droplets flowed along the microchannel 1. Once the flow was steady, the outlet 6 was opened while at the same time the outlet 4 was closed. A few hundred droplets were therefore immobilized in the microchannel 1.

The temperature of the sheet was controlled using a Peltier module (Melcor, 62×62 $mm^2$ in size) and water circulation from a cryostat, both items being placed immediately beneath the plate. The syringe containing the aqueous solution and the corresponding linking tube were heated to above the solubility temperature of the solution using flexible (Minco) heaters so as to avoid any inopportune crystallization. Four thermocouples (Thermocoax), which were inserted through the PDMS layer as far as the silicon plate, took temperature measurements close to the microchannel 1. The large size of the Peltier module gave a uniform temperature field along the storage zone, with temperature differences of less than 0.1° C.

Images of crystallization occurring in the droplets were taken using a binocular microscope and a CCD camera. The number of crystals was easy recorded, thanks to the birefringence of the $KNO_3$ crystals, which appeared as bright pixels, under the effect of crosspolarizers. At the magnification used, the detectable crystal size was about 500 μm.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of monitoring the crystallization of a substance in solution in a solvent, comprising the following steps:
    forming droplets of said solution, optionally with different concentrations of said substance, in an inert phase;
    storing the droplets produced in at least one storage microchannel;
    forming crystals in all of the droplets;
    increasing the temperature to dissolve at least certain of the crystals in at least certain droplets; and
    observing and analyzing the crystallization and dissolution sequence.

2. The method as defined by claim 1, wherein the step of forming droplets of said solution in an inert phase is performed at a temperature above the solubility temperature of said substance.

3. The method as defined by claim 1, wherein the step of forming crystals in all of the droplets comprises cooling said droplets below the solubility temperature thereof.

4. The method as defined by claim 1, wherein the step of analyzing the crystallization and dissolution sequence is carried out using Raman spectroscopy or optical microscopy.

5. The method as defined by claim 1, further comprising observing the structure of the crystals formed during the crystallization, optionally by Raman spectroscopy.

6. The method as defined by claim 1, further comprising determining polymorphism by observing at least two different crystalline structures for the same substance.

7. The method as defined by claim 1, wherein in the step of forming droplets of said solution in an inert phase, at least one hundred droplets are formed.

8. The method as defined by claim 1, wherein in the step of forming droplets of said solution in an inert phase, the volume of each droplet formed is small enough to induce a single-nucleation crystallization mechanism in at least most of the droplets.

9. The method as defined by claim 8, wherein the volume of each droplet formed is less than 1 μl.

10. The method as defined by claim 1, wherein the inert phase comprises a silicone oil or a fluorinated oil.

11. The method as defined by claim 1, wherein the solubility of said substance is measured as a function of the temperature of a metastable polymorph or of several polymorphs at the same time.

12. The method as defined by claim 1, wherein the temperature of the droplets is lowered and/or raised in steps.

13. The method as defined by claim 12, wherein the temperature difference ($\Delta T$) per step ranges from 0.1 to 5° C.

14. The method as defined by claim 12, wherein the number of steps ranges from 10 to 50.

15. The method as defined by claim 1, wherein a first temperature ($T_{min}$), at which all the crystals are formed, is identified.

16. The method as defined by claim 15, wherein the temperature is lowered in steps[, the number of crystals for different temperature values is counted and said first temperature ($T_{min}$) is determined as being the temperature below which no additional crystal is formed.

17. The method as defined by claim 1, wherein a second temperature ($T_{max}$), for which all the crystals are dissolved, is identified.

18. The method as defined by claim 17, wherein the temperature is increased in steps, the number of crystals for increasingly higher temperatures is counted and said second temperature ($T_{max}$) is identified, this being the temperature above which no additional crystal dissolves.

19. A method of screening several substances, wherein said several substances are prepared, the crystallization of each substance is monitored via the method as defined by claim 1, and at least one preferred substance, among said several substances, is identified.

20. The method as defined by claim 19, wherein said several substances are prepared by modifying at least one parameter of these substances, selected from the pH, the presence of impurities or the presence of at least one adjuvant.

21. The method as defined by claim 19, wherein said several substances are formed from a mixture of at least two components and said different substances are prepared by modifying the proportion of these components.

* * * * *

UNITED STATES PATENT AND TRADEMARK OFFICE
CERTIFICATE OF CORRECTION

| | | |
|---|---|---|
| PATENT NO. | : 8,053,242 B2 | Page 1 of 1 |
| APPLICATION NO. | : 12/553557 | |
| DATED | : November 8, 2011 | |
| INVENTOR(S) | : Joanicot et al. | |

It is certified that error appears in the above-identified patent and that said Letters Patent is hereby corrected as shown below:

Title Page, Item 73 (Assignee:) please add --Centre National de la Recherche Scientifique (C.N.R.S.), Paris (FR)--.

Signed and Sealed this
Twenty-third Day of October, 2012

David J. Kappos
*Director of the United States Patent and Trademark Office*